US010654859B2

(12) United States Patent
Wang et al.

(10) Patent No.: US 10,654,859 B2
(45) Date of Patent: May 19, 2020

(54) METHANESULFONATE POLYMORPH OF 5-TYPE PHOSPHODIESTERASE INHIBITOR AND PREPARATION METHOD AND APPLICATIONS THEREOF (71) Applicant: JINAN MEILUWEI BIOTECHNOLOGY CO., LTD., Jinan, Shandong (CN)

(72) Inventors: Jinglin Wang, Jinan (CN); Ruimei Yu, Jinan (CN); Qiongqiong Lian, Jinan (CN)

(73) Assignee: JINAN MEILUWEI BIOTECHNOLOGY CO., LTD., Shandong (CN)

( * ) Notice: Subject to any disclaimer, the term of this patent is extended or adjusted under 35 U.S.C. 154(b) by 0 days.

(21) Appl. No.: 16/317,208

(22) PCT Filed: Jul. 26, 2017

(86) PCT No.: PCT/CN2017/094467
§ 371 (c)(1),
(2) Date: Jan. 11, 2019

(87) PCT Pub. No.: WO2018/209809
PCT Pub. Date: Nov. 22, 2018

(65) Prior Publication Data
US 2019/0292192 A1   Sep. 26, 2019

(30) Foreign Application Priority Data
May 19, 2017   (CN) .......................... 2017 1 0361203

(51) Int. Cl.
*C07D 487/04*   (2006.01)
(52) U.S. Cl.
CPC ........ *C07D 487/04* (2013.01); *C07B 2200/13* (2013.01)
(58) Field of Classification Search
CPC .................... C07D 487/04; C07B 2200/13
See application file for complete search history.

(56) References Cited

FOREIGN PATENT DOCUMENTS

| CN | 1240134 A | 1/2000 | |
| CN | 101343275 A | 1/2009 | |
| CN | 104650093 A | * 2/2015 | ........... C07D 487/04 |
| CN | 104650093 A | 5/2015 | |
| WO | 2005/077374 A1 | 8/2005 | |

OTHER PUBLICATIONS

Feb. 22, 2018 International Search Report issued in International Patent Application No. PCT/CN2017/094467.
Yuan-Feng et al; "Study on the synthesis technology of sildenafil analogues," China Modern Medicine; vol. 21; No. 5; pp. 15-17; Feb. 28, 2014.
Lebel et al; "A rapid, quantitative liquid chromatography-mass spectrometry screening method for 71 active and 11 natural erectile dysfunction ingredients present in potentially adulterated or counterfeit products;" Journal of Chromatography A; No. 1343; pp. 143-151; Apr. 4, 2014.
Feb. 22, 2018 Written Opinion issued in International Patent Application No. PCT/CN2017/094467.

* cited by examiner

*Primary Examiner* — Erich A Lesser
(74) *Attorney, Agent, or Firm* — Oliff PLC (57) ABSTRACT

A methanesulfonate polymorph of a 5-type phosphodiesterase inhibitor. The structure of the 5-type phosphodiesterase inhibitor is as shown in formula A:

Formula A

The methanesulfonate polymorph of the 5-type phosphodiesterase inhibitor includes the following diffraction peaks measured at 2θ reflection angles in an X-ray powder diffraction pattern: 7.1750°±0.2°, 7.6299°±0.2°, 8.8588°±0.2°, 13.2310°±0.2°, 14.3754°±0.2°, 14.8440±0.2°, 15.2941°±0.2°, 17.1838°±0.2°, 20.0314°±0.2°, 20.8507°±0.2°, 21.2839°±0.2°, 21.7890°±0.2°, 22.2594°±0.2°, 23.0373±0.2°, 25.1243°±0.2°, 25.4244°±0.2°, 26.1530°±0.2°, 28.1210°±0.2°, 30.0135°±0.2°, 31.4809°±0.2°, 32.3619°±0.2°, 37.2410°±0.2°, 37.6388°±0.2° and 40.8286°±0.2°. The methanesulfonate of the 5-type phosphodiesterase inhibitor not only improves the activity of drugs, but also improves the water solubility and the bioavailability of the drugs, and makes up the blank of studies on drugs of the crystal form.

11 Claims, 3 Drawing Sheets

METHANESULFONATE POLYMORPH OF 5-TYPE PHOSPHODIESTERASE INHIBITOR AND PREPARATION METHOD AND APPLICATIONS THEREOF

FIELD OF THE INVENTION

The present invention relates to the technical field of crystalline compounds, and specifically relates to a methanesulfonate polymorph of a 5-type phosphodiesterase inhibitor, a preparation method and applications thereof.

BACKGROUND OF THE INVENTION

Erectile dysfunction (ED) refers to the inability to persistently reach and/or maintain a full erection for satisfactory sexual life. According to statistics, about 150 million men worldwide have different degrees of ED symptoms, and it is predicted that the number of such patients will double by 2025. PDE5 (5-type phosphodiesterase) inhibitors are the most mature ED therapeutic drugs currently studied. Five of such drugs approved for marketing today are sildenafil, tadanafil, vardenafil, udenafil and mirodenafil. It has been reported in the literature that such compounds have strong selective inhibition on phosphodiesterase, which has attracted wide attention and become a new research hotspot. Related studies have carried out extensive structural modifications to such compounds in order to improve their activity and selectivity to phosphodiesterase 5.

A series of sildenafil analogues synthesized have been reported in the literature, among which, Da Yuanfeng et al. (Study on Synthesis of Sildenafil Analogue, China Contemporary Medicine, Vol. 21, No. 5, February 2014) synthesized a sildenafil analogue (WG001), the chemical name of which is 5-[2-ethoxy-5-(4-methylpiperazin-1-ylthiocarbonyl)phenyl]-1-methyl-3-n-propyl-1,6-dihydro-pyrazolo[4,3-d]pyrimidin-7-thione, and the structural formula is as follows:

The Chinese patent "Synthesis Method of Sildenafil Analogue" (CN104650093A) improves the above synthesis method of the sildenafil analogue, and details the preparation method of the sildenafil analogue.

The crystal form is a different solid state formed by arranging compound molecules or atoms differently in a lattice space. Different crystal forms of the same drug may have significant differences in stability, bioavailability and the like, thereby affecting the efficacy of the drug. Therefore, the study on the crystal form of a drug is an important part of the research on the material basis of drugs, but no crystal form of 5-[2-ethoxy-5-(4-methylpiperazin-1-ylthiocarbonyl)phenyl]-1-methyl-3-n-propyl-1,6-dihydro-pyrazolo[4,3-d]pyrimidin-7-thione methanesulfonate drugs has been reported at present. Moreover, the sildenafil analogue has some drawbacks in drug metabolism, and the bioavailability needs to be further improved.

SUMMARY OF THE INVENTION

In view of the above prior art, the object of the present invention is to provide a methanesulfonate polymorph of a 5-type phosphodiesterase inhibitor and a preparation method and applications thereof, which can improve the activity and bioavailability of the drug.

In order to achieve the above object, the present invention adopts the following technical solution:

In a first aspect of the present invention, provided is a methanesulfonate polymorph of a 5-type phosphodiesterase inhibitor, the structure of the 5-type phosphodiesterase inhibitor being as shown in formula A:

Formula A

Figure 1:
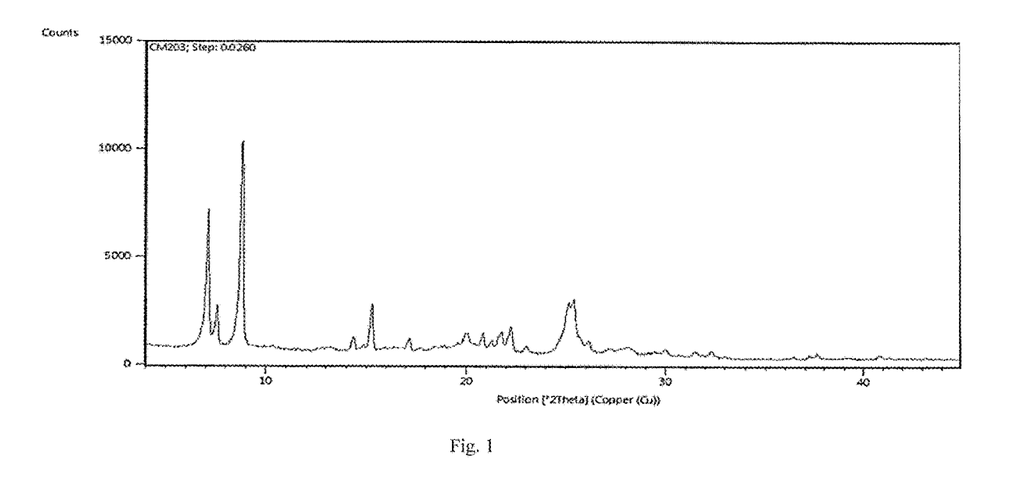
FIG. 1 is an X-ray powder diffraction pattern of a methanesulfonate polymorph of a compound of formula A.

The X-ray powder diffraction pattern of the methanesulfonate polymorph of the 5-type phosphodiesterase inhibitor is shown in FIG. 1.

The methanesulfonate polymorph of the 5-type phosphodiesterase inhibitor includes the following diffraction peaks measured at 2θ reflection angles in the X-ray powder diffraction pattern: 7.1750°±0.2°, 7.6299°±0.2°, 8.8588°±0.2°, 13.2310°±0.2°, 14.3754°±0.2°, 14.8440°±0.2°, 15.2941°±0.2°, 17.1838°±0.2°, 20.0314°±0.2°, 20.8507°±0.2°, 21.2839°±0.2°, 21.7890°±0.2°, 22.2594°±0.2°, 23.0373±0.2°, 25.1243°±0.2°, 25.4244°±0.2°, 26.1530°±0.2°, 28.1210°±0.2°, 30.0135°±0.2°, 31.4809°±0.2°, 32.3619°±0.2°, 37.2410°±0.2°, 37.6388°±0.2°, 40.8286°±0.2°.

Figure 2:
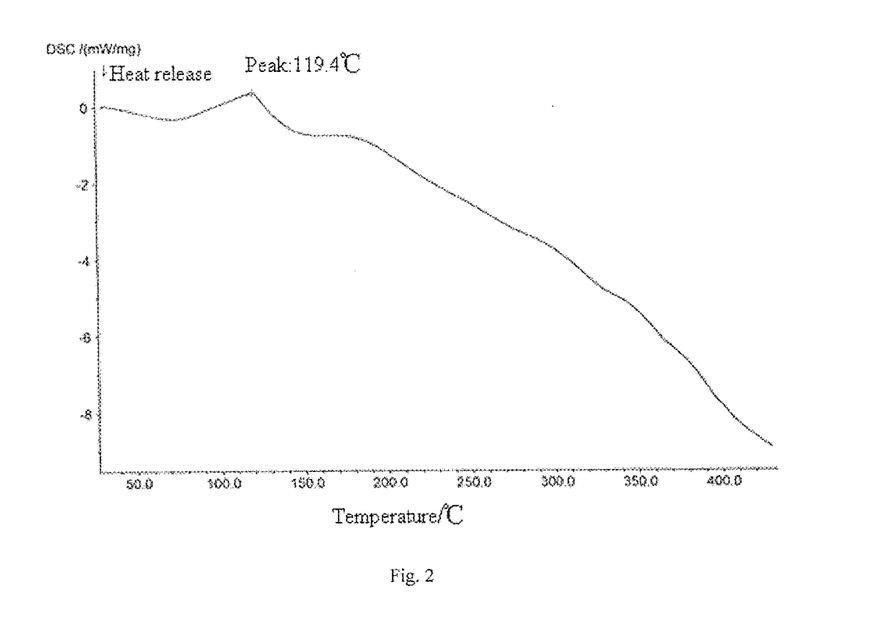
FIG. 2 is a thermal analysis diagram of a methanesulfonate polymorph of a compound of formula A.
Figure 3:
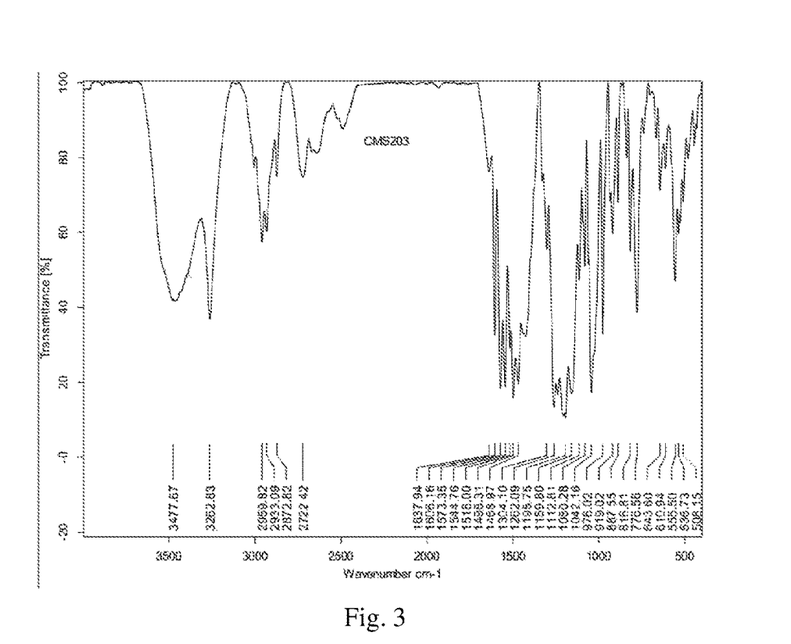
FIG. 3 is an IR spectrogram of the methanesulfonate polymorph of the compound of formula A.

In addition, the present invention also analyzes the methanesulfonate polymorph of the 5-type phosphodiesterase inhibitor by differential scanning calorimetry and infrared spectroscopy, the differential scanning calorimetry diagram is shown in FIG. 2, and the infrared spectrogram is shown in FIG. 3.

In a second aspect of the present invention, provided is a preparation method of the above methanesulfonate polymorph of a 5-type phosphodiesterase inhibitor, comprising the steps of: preparing a methanesulfonate of a 5-type phosphodiesterase inhibitor; and dissolving the methanesulfonate of the 5-type phosphodiesterase inhibitor into anhydrous ethanol, performing filter pressing after the solid is completely dissolved, cooling the filtrate to a temperature of 20° C. or lower and standing for crystallization.

In the above preparation method, the step of preparing a methanesulfonate of a 5-type phosphodiesterase inhibitor is specifically: adding a compound of formula A to anhydrous ethanol, stirring uniformly, slowly adding 5% NaOH, stirring, performing suction filtration at a temperature of 10° C. or lower after the solid is completely dissolved, adding a mixed solution of methanesulfonic acid and anhydrous ethanol to the filtrate, adjusting the pH value to 7-8, stirring and crystallizing to precipitate a solid; performing suction filtration, adding the solid to anhydrous ethanol, heating to 30-35° C., adjusting the pH value to 3-4 with methanesulfonic acid, heating to 80° C., refluxing, then slightly cooling to 70° C., performing suction filtration while hot, naturally cooling the filtrate to room temperature, then cooling the filtrate to 15° C. or lower with ice water, standing for crystallization, performing suction filtration, and drying the solid at 80-90° C. to obtain a methanesulfonate of a phosphodiesterase 5-type inhibitor.

In the above preparation method, the methanesulfonate of the 5-type phosphodiesterase inhibitor is dissolved in 3 times by weight of anhydrous ethanol and heated to 50-60° C., the pH value is adjusted to 3-4 with methanesulfonic acid, and then the mixed solution is heated to 70-75° C. so that the solid is completely dissolved.

In a third aspect of the present invention, provided is an application of the above methanesulfonate polymorph of the 5-type phosphodiesterase inhibitor in preparation of a drug for treating or preventing male erectile dysfunction.

Further, the present invention provides an application of the above methanesulfonate polymorph of the 5-type phosphodiesterase inhibitor in preparation of drugs for treating or preventing diseases related to 5-type phosphodiesterase.

The diseases related to 5-type phosphodiesterase include: male sexual dysfunction, female sexual dysfunction, benign prostatic hyperplasia, bladder obstruction, incontinence, angina pectoris, hypertension, pulmonary hypertension, congestive heart failure, arteriosclerosis, stroke, peripheral circulatory system disease, asthma, bronchitis, Alzheimer's disease, acute respiratory failure, etc.

In a fourth aspect of the present invention, provided is a pharmaceutical composition for treating or preventing male erectile dysfunction, comprising an effective amount of the above methanesulfonate polymorph of the 5-type phosphodiesterase inhibitor.

The above pharmaceutical composition can be formulated into solid oral preparations such as tablets, capsules, pills and powder, or liquid oral preparations such as suspending agents, dissolving agents, emulsions and syrups. These preparations may contain conventional functional excipients such as wetting agents, sweeteners, flavoring agents and preservatives, or contain conventional functional excipients such as fillers, binders, dispersants, diluents, absorption enhancers, absorbents and lubricants, or be made into a paste for external use, and is also suitable for being made into intravenous injections.

In a fifth aspect of the present invention, provided is a pharmaceutical composition for treating or preventing diseases related to 5-type phosphodiesterase, comprising an effective amount of the above methanesulfonate polymorph of the 5-type phosphodiesterase inhibitor.

The above technical solution has the following beneficial effects:

The 5-type phosphodiesterase inhibitor of formula A is used as a research object in the present invention and first forms a salt with methanesulfonic acid to obtain a methanesulfonate of the 5-type phosphodiesterase inhibitor, then the methanesulfonate is crystallized through a solvent, and a methanesulfonate polymorph of a 5-type phosphodiesterase inhibitor better in treating male erectile dysfunction and diseases related to 5-type phosphodiesterase is further obtained, which not only improves the activity of drugs, but also improves the water solubility and the bioavailability of the drugs, and makes up the blank of studies on drugs of the crystal form.

BRIEF DESCRIPTION OF THE DRAWINGS

The accompanying drawings constituting a part of the present application are used for further understanding the present application, and the schematic embodiments of the present application and the description thereof are used for interpreting the present application, rather than constituting improper limitation to the present application.

DETAILED DESCRIPTION OF THE EMBODIMENTS

It should be pointed out that the following detailed descriptions are all exemplary and aim to further illustrate the present invention. Unless otherwise specified, all technical and scientific terms used in the descriptions have the same meanings as generally understood by those of ordinary skill in the art of the present invention.

It should be noted that the terms used herein are merely for describing specific embodiments, but are not intended to limit exemplary embodiments according to the present invention. As used herein, unless otherwise explicitly pointed out in the context, the singular form is also intended to include the plural form. In addition, it should also be understood that when the terms "include" and/or "comprise" are used in the specification, they indicate features, steps, operations and/or their combinations.

As described in the background, no crystal form of 5-[2-ethoxy-5-(4-methylpiperazin-1-ylthiocarbonyl)phenyl]-1-methyl-3-n-propyl-1,6-dihydro-pyrazolo[4,3-d]pyrimidin-7-thione methanesulfonate drugs has been reported at present; and the sildenafil analogue has some drawbacks in drug metabolism, and the bioavailability needs to be further improved. Based on this, the present invention proposes a methanesulfonate polymorph of a 5-type phosphodiesterase inhibitor, a preparation method and application thereof.

In one embodiment of the present application, a methanesulfonate polymorph of a 5-type phosphodiesterase inhibitor is provided, and the methanesulfonate polymorph is a novel crystal structure capable of improving the water solubility and bioavailability of the 5-type phosphodiesterase inhibitor.

The X-ray powder diffraction pattern of the methanesulfonate polymorph of the 5-type phosphodiesterase inhibitor is shown in FIG. 1. The detailed powder X-ray diffraction parameters of the new crystal form are shown in Table 1.

TABLE 1

Powder X-ray diffraction peaks of the new crystal form according to the present invention

| Peak Number | Pos. [°2Th.] | Height [cts] | FWHMLeft [°2Th.] | d-spacing [Å] | Rel. Int. [%] |
|---|---|---|---|---|---|
| 1 | 7.1750 | 6268.30 | 0.1279 | 12.32069 | 65.29 |
| 2 | 7.6299 | 1937.65 | 0.1023 | 11.58704 | 20.18 |
| 3 | 8.8588 | 9600.82 | 0.1279 | 9.98228 | 100.00 |
| 4 | 13.2310 | 143.02 | 0.4093 | 6.69181 | 1.49 |
| 5 | 14.3754 | 602.81 | 0.1279 | 6.16156 | 6.28 |
| 6 | 14.8440 | 225.97 | 0.1023 | 5.96809 | 2.35 |
| 7 | 15.2941 | 2060.93 | 0.1279 | 5.79345 | 21.47 |
| 8 | 17.1838 | 531.85 | 0.1279 | 5.16038 | 5.54 |
| 9 | 20.0314 | 681.97 | 0.2047 | 4.43276 | 7.10 |
| 10 | 20.8507 | 722.79 | 0.1023 | 4.26040 | 7.53 |
| 11 | 21.2839 | 396.81 | 0.1279 | 4.17466 | 4.13 |
| 12 | 21.7890 | 800.13 | 0.1279 | 4.07901 | 8.33 |
| 13 | 22.2594 | 1053.90 | 0.1279 | 3.99386 | 10.98 |
| 14 | 23.0373 | 300.40 | 0.1279 | 3.86073 | 3.13 |
| 15 | 25.1243 | 2211.44 | 0.2303 | 3.554456 | 23.03 |
| 16 | 25.4244 | 2352.21 | 0.1535 | 3.50340 | 24.50 |
| 17 | 26.1530 | 471.66 | 0.1023 | 3.40743 | 4.91 |
| 18 | 28.1210 | 236.79 | 0.4093 | 3.17329 | 2.47 |
| 19 | 30.0135 | 250.06 | 0.2303 | 2.97737 | 2.60 |
| 20 | 31.4809 | 194.85 | 0.2047 | 2.84185 | 2.03 |
| 21 | 32.3619 | 285.13 | 0.1279 | 2.76647 | 2.97 |
| 22 | 37.2410 | 152.91 | 0.1535 | 2.41447 | 1.59 |
| 23 | 37.6388 | 194.92 | 0.1535 | 2.38986 | 2.03 |
| 24 | 40.8286 | 162.03 | 0.2047 | 2.21022 | 1.69 |

In addition, the present invention also analyzes the methanesulfonate polymorph of the 5-type phosphodiesterase inhibitor by differential scanning calorimetry and infrared spectroscopy, the differential scanning calorimetry diagram is shown in FIG. 2, and the diagram shows one endothermic peak at 119.4° C.

The infrared spectrogram is shown in FIG. 3, and shows infrared spectral characteristic peaks at 3477.67 cm$^{-1}$, 3262.83 cm$^{-1}$, 2959.82 cm$^{-1}$, 2933.09 cm$^{-1}$, 2872.82 cm$^{-1}$, 2722.42 cm$^{-1}$, 1637.94 cm$^{-1}$, 1606.16 cm$^{-1}$, 1573.35 cm$^{-1}$, 1544.76 cm$^{-1}$, 1518.00 cm$^{-1}$, 1498.31 cm$^{-1}$, 1468.97 cm$^{-1}$, 1304.10 cm$^{-1}$, 1262.09 cm$^{-1}$, 1195.75 cm$^{-1}$, 1112.81 cm$^{-1}$, 1080.28 cm$^{-1}$, 1042.16 cm$^{-1}$, 976.02 cm$^{-1}$, 919.02 cm$^{-1}$, 887.55 cm$^{-1}$, 816.81 cm$^{-1}$, 776.56 cm$^{-1}$, 643.60 cm$^{-1}$, 610.94 cm$^{-1}$, 555.50 cm$^{-1}$, 536.73 cm$^{-1}$ and 508.15 cm$^{-1}$. In another embodiment of the present invention, a pharmaceutical composition is composed of an effective amount of the methanesulfonate polymorph of the 5-type phosphodiesterase inhibitor according to the present invention and pharmaceutically acceptable excipients together.

The effective amount described in the present invention refers to a dose of a pharmacological agent capable of achieving a therapeutic effect. The pharmaceutically acceptable excipients may be conventional functional excipients such as wetting agents, sweeteners, flavoring agents and preservatives, or conventional functional excipients such as fillers, binders, dispersants, diluents, absorption enhancers, absorbents and lubricants.

In order that those skilled in the art can understand the technical solution of the present invention more clearly, the technical solutions of the present invention will be described in detail below in combination with specific embodiments.

The compound of formula A in the embodiment of the present invention is an existing compound in the prior art, can be synthesized by the method in "Study on Synthesis of Sildenafil Analogue" (China Contemporary Medicine, Vol. 21, No. 5, February 2014), and can also be synthesized by the method in the patent "Synthesis Method of Sildenafil Analogue" (CN104650093A).

Embodiment 1: Preparation of 5-[2-ethoxy-5-(4-methylpiperazin-1-ylthiocarbonyl)phenyl]-1-methyl 3-n-propyl-1,6-dihydro-pyrazolo[4,3-d]pyrimidin-7-thione methanesulfonate polymorph The specific preparation method is as follows:

200 g of anhydrous ethanol and 100 g of the compound of formula A are put into a cleaned and dried reaction flask and stirred uniformly, and then 200 g of 5% NaOH is slowly added. The compound of formula A is completely dissolved while stirring. After the solid is completely dissolved, suction filtration is performed at 10° C. or below (this condition must be 10° C. or below), a mixed solution of 20 g of methanesulfonic acid and 80 g of anhydrous ethanol is added to the filtrate to adjust the pH value to 7-8, preferably 8 (note: cooled with ice water), the solid is re-precipitated and the mixture is crystallized for 2 h while stirring. Suction filtration is performed, the solid is added to 320 g of anhydrous ethanol, the solution is heated to 30-35° C., the pH value is adjusted with methanesulfonic acid (about 22 g), the solid is gradually dissolved and the temperature rises, then the solid is completely dissolved, the pH value of the solution is maintained to 3-4, closer to 3 (not more than 60° C.), and the solution is stirred for 10 min after the adjustment, heated to 80° C. after the pH value (3-4, closer to 3) is stable, and refluxed for 1 h. The solution is slightly cooled to 70° C. and subjected to suction filtration while hot. The filtrate is naturally cooled to room temperature and then cooled to 15° C. or lower with ice water. The filtrate is placed for crystallizing 2 h and subjected to suction filtration, and the solid is dried at 80-90° C. to obtain the methanesulfonate of the compound of formula A.

The methanesulfonate of the compound of formula A is added to 3 times ethanol and heated to 50-60° C., the pH value is adjusted with methanesulfonic acid to 3-4, closer to 3, then the solution is heated to 70-75° C., the solid is completely dissolved, the solution is subjected to filter pressing while hot, the filtrate is cooled to 20° C. or lower and stood for crystallizing 10 h, and is centrifuged, and the solid is dried. A methanesulfonate polymorph of the compound of formula A is obtained.

The obtained methanesulfonate polymorph of the compound of formula A is detected at room temperature using an empyrean X-ray diffractometer of the Netherlands PANalytical B.V, and 2θ angle scanning is carried out from 5° to 40°, Cu-Kα, the scanning speed being 2°/min, the tube voltage being 40 kv, and the tube current being 40 mA.

The X-ray powder diffraction pattern of the polymorph is shown in FIG. 1. The diffraction peaks at the 2θ values of the polymorph include: 7.1750°±0.2°, 7.6299°±0.2°, 8.8588°±0.2°, 13.2310°±0.2°, 14.3754°±0.2°, 14.4840±0.2°, 15.2941°±0.2°, 17.1838°±0.2°, 20.0314°±0.2°, 20.8507°±0.2°, 21.2839°±0.2°, 21.7890°±0.2°, 22.2594°±0.2°, 23.0373±0.2°, 25.1243°±0.2°, 25.4244°±0.2°, 26.1530°±0.2°, 28.1210°±0.2°, 30.0135°±0.2°, 31.4809°±0.2°, 32.3619°±0.2°, 37.2410°±0.2°, 37.6388°±0.2°, 40.8286°±0.2°.

The obtained methanesulfonate polymorph of the compound of formula A is detected by a STA449F3 differential scanning calorimeter of NETZSCH, the gas being high argon, the heating rate being 10° C./min, and the scanning temperature range being 30° C.-400° C.

The thermal analysis diagram of the polymorph is shown in FIG. 2, with its maximum endothermal value at 119.4° C.

The obtained methanesulfonate polymorph of the compound of formula A is detected by a VERTEX 70 infrared spectrometer of BRUKER at room temperature, the spectral range being a wave number of 4000-400 cm$^{-1}$.

The infrared spectrogram of the polymorph is shown in FIG. 3.

The content of the methanesulfonate polymorph of the compound of formula A is detected by liquid chromatography, and the detection condition is as follows:

(1) Sample treatment: The sample is dissolved in methanol to obtain a sample having a concentration of 500 μg/ml.

(2) Chromatographic condition: detection wavelength: 285 nm; mobile phase composition: acetonitrile: 0.1% phosphoric acid; elution condition: gradient elution, gradual change from 20:80 to 25:75 in 0-15 min, and gradual change from 25:75 to 40:60 in 15-20 min. Column temperature: 30.1° C.; flow rate 1 ml/min; sample amount 20 μL.

Figure 4:
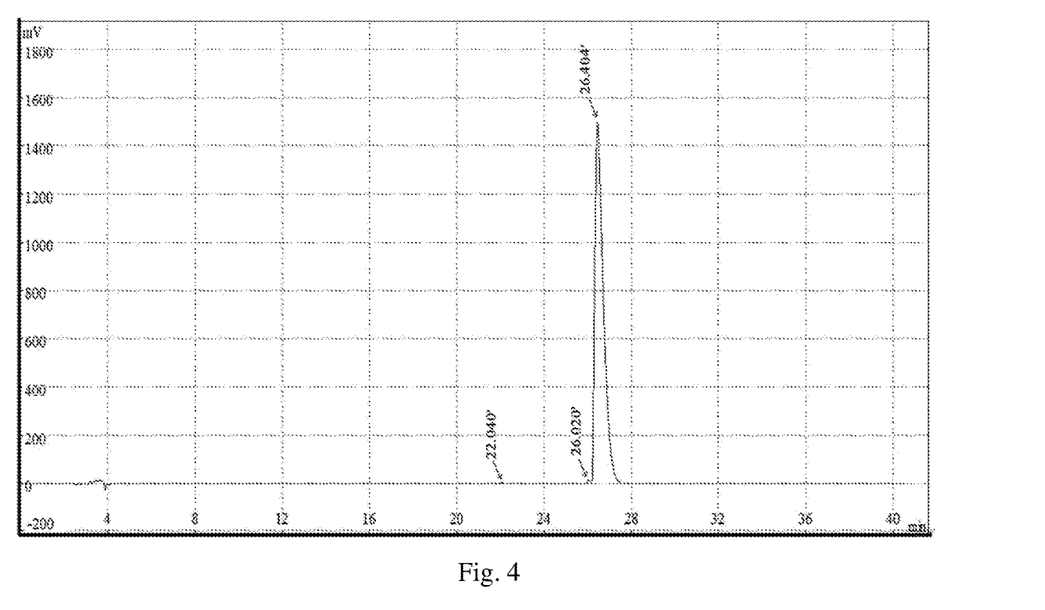
FIG. 4 is a liquid chromatogram of the methanesulfonate polymorph of the compound of formula A.

The chromatogram of content determination is shown in FIG. 4. The chromatographic data is shown in Table 2.

TABLE 2

Chromatographic data

| Retention Time | Component Name | Concentration | Peak Area | Peak Height | Half Peak Width |
|---|---|---|---|---|---|
| 22.04 | | 0.223 | 90042 | 8516 | 9.929 |
| 26.02 | | 0.2608 | 105301 | 11604 | 8.522 |
| 26.404 | Methanesulfonate of compound of formula A | 99.51 | 40176899 | 1498970 | 25.171 |

By calculation, the molar yield is 90% and the purity is 99.51%.

Test Example 1: Solubility Test

The regulations on solubility in the guide to the second volume of Chinese Pharmacopoeia 2010 edition are used as criteria.

Weigh samples ground to fine powder (sample B: the compound of formula A; sample C: the methanesulfonate polymorph of the compound of formula A prepared in Embodiment 1), put the samples into a certain volume of solvent at 25° C.±2° C., and vigorously shake the samples for 30 seconds every 5 minutes; observe the dissolution within 30 minutes, wherein if solute particles are not observed, the samples are completely dissolved.

1 g of sample B is not dissolved in 10000 g of water, so the sample B is hardly soluble in water.

1 g of sample C is completely dissolved in 800 g of water, so the sample C is slightly soluble in water.

1 g of sample B is not completely dissolved in 10000 g of 95% ethanol, so the sample B is almost insoluble in 95% ethanol.

1 g of sample C is completely dissolved in 90 g of 95% ethanol, so the sample C is slightly soluble in 95% ethanol.

Test Example 2: Bioavailability Test

By determining the plasma concentrations of SD rats intragastrically administered with B (a reference preparation, the compound of formula A being an active ingredient) or C (a tested preparation, the methanesulfonate polymorph of the compound of formula A prepared in Embodiment 1 being an active ingredient) capsule contents, the main pharmacokinetic parameters are counted, and the relative bioavailability (F) of the two preparations is calculated.

1. Test Method:

12 male SD rats are randomly divided into two groups according to the weight, with 6 rats in each group. After being fasted for about 12 h, each of the two groups of rats is intragastrically administered with 50 mg of a solution of B or C capsule contents (based on the compound content shown in formula A). Blood is collected before each group is administered, and 0.5 mL of blood is collected from the eyelid at 0.5, 1, 2, 3, 4, 6, 8, 24, 32 and 48 h after the administration, put into heparin sodium anti-coagulated centrifuge tubes, and centrifuged for 5 min at 4° C. under 12000 r/m to prepare plasma. The content of A in the rat plasma is detected by HPLC-MS/MS. The plasma concentration-time data of A is processed by a DAS 3.2.6 program, and the pharmacokinetic parameters of each group are calculated.

Figure 5:
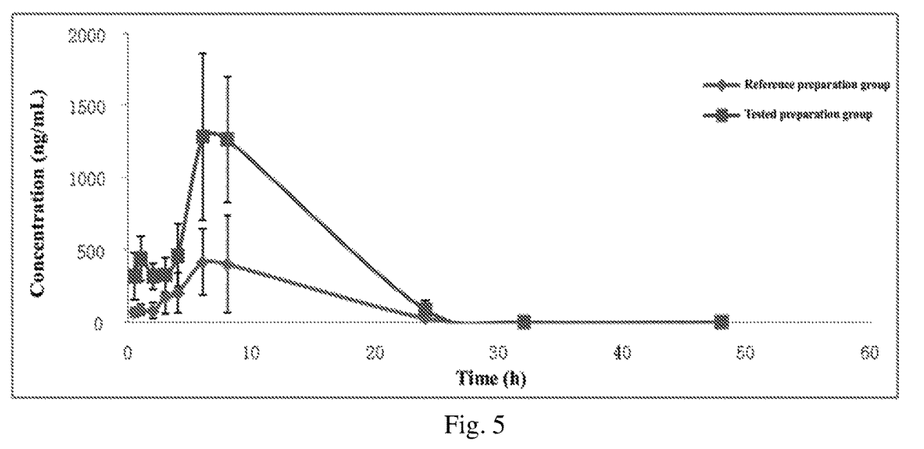
FIG. 5 is average plasma concentration-time curves after intragastric administration of B and C capsule contents in a reference preparation group and a tested preparation group.
Figure 6:
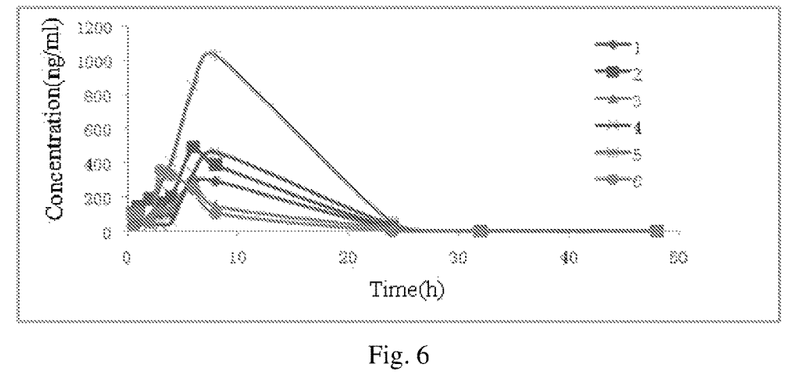
FIG. 6 is individual plasma concentration-time curves after intragastric administration of B capsule contents to SD rats in the reference preparation group.
Figure 7:
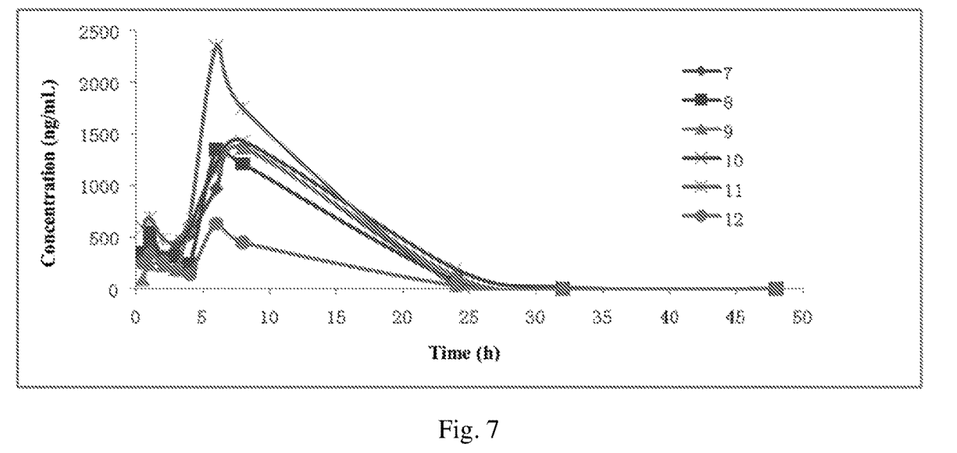
FIG. 7 is individual plasma concentration-time curves after intragastric administration of C capsule contents to SD rats in the tested preparation group.

2. Test Results:

After the SD rats are intragastrically administered with the capsule contents of the reference preparation B and the tested preparation C respectively, the average plasma concentration-time curves and the individual plasma concentration-time curves of the compound of formula A are shown in FIGS. 5-7; the average plasma concentration and the individual plasma concentration are shown in Tables 3-6.

The main pharmacokinetic parameters of the compound of formula A of the reference preparation and tested preparation groups are shown in Tables 7 and 8. The analysis results of the two groups of pharmacokinetic parameters by double unilateral T inspection are shown in Table 9.

TABLE 3

Average plasma concentration (μg/L)-time (h) data of the compound of formula A after the SD rats in the reference preparation group are intragastrically administered with B capsule contents

| Time (h) | Compound of formula A (μg/L) |
|---|---|
| 0 | — |
| 0.5 | 70.00 ± 29.60 |
| 1 | 86.05 ± 35.95 |
| 2 | 79.48 ± 54.57 |
| 3 | 177.08 ± 117.28 |
| 4 | 204.18 ± 136.72 |
| 6 | 418.33 ± 229.33 |
| 8 | 403.33 ± 335.61 |
| 24 | 29.10 ± 16.37 |
| 32 | — |
| 48 | — |

—, the detected value is lower than the minimum quantification limit (1 μg/L).

TABLE 4

Average plasma concentration (μg/L)-time (h) data after the SD rats in the tested preparation group are intragastrically administered with C capsule contents

| Time (h) | Compound of formula A (μg/L) |
|---|---|
| 0 | — |
| 0.5 | 318.43 ± 160.92 |
| 1 | 440.50 ± 157.12 |
| 2 | 316.83 ± 88.43 |
| 3 | 328.00 ± 119.34 |
| 4 | 459.50 ± 216.65 |
| 6 | 282.17 ± 579.55 |
| 8 | 1263.50 ± 435.91 |
| 24 | 87.00 ± 61.52 |
| 32 | 2.87 ± 7.02 |
| 48 | — |

—, the detected value is lower than the minimum quantification limit (1 μg/L).

TABLE 5

Plasma concentration (μg/L)-time (h) data of the compound of formula A after the SD rats in the reference preparation group are intragastrically administered with B capsule contents

| Time (h) | No 1 | No 2 | No 3 | No 4 | No 5 | No 6 |
|---|---|---|---|---|---|---|
| 0 | — | — | — | — | — | — |
| 0.5 | 45.1 | 109 | 35.7 | 59.9 | 69.3 | 101 |
| 1 | 43.9 | 145 | 71.9 | 74 | 70.5 | 111 |
| 2 | 69.9 | 189 | 65.8 | 43.8 | 60 | 48.4 |
| 3 | 98.9 | 165 | 131 | 38.6 | 273 | 356 |
| 4 | 102 | 196 | 141 | 53.1 | 408 | 325 |
| 6 | 295 | 491 | 284 | 340 | 853 | 247 |
| 8 | 292 | 387 | 147 | 459 | 1030 | 105 |
| 24 | 17.1 | 20.4 | 16 | 38.6 | 53.4 | — |
| 32 | — | — | — | — | — | — |
| 48 | — | — | — | — | — | — |

—, the detected value is lower than the minimum quantification limit (1 μg/L).

TABLE 6

Plasma concentration (μg/L)-time (h) data of the compound of formula A after the SD rats in the tested preparation group are intragastrically administered with C capsule contents

| Time (h) | No 7 | No 8 | No 9 | No 10 | No 11 | No 12 |
|---|---|---|---|---|---|---|
| 0 | — | — | — | — | — | — |
| 0.5 | 312 | 348 | 97.6 | 307 | 593 | 253 |
| 1 | 445 | 544 | 244 | 382 | 687 | 341 |
| 2 | 319 | 301 | 227 | 310 | 483 | 261 |
| 3 | 429 | 314 | 193 | 390 | 460 | 182 |
| 4 | 523 | 239 | 588 | 578 | 686 | 143 |
| 6 | 970 | 1350 | 1180 | 1210 | 2350 | 633 |
| 8 | 1370 | 1210 | 1370 | 1430 | 1750 | 451 |
| 24 | 71 | 78.4 | 122 | 191 | 27.7 | 31.9 |
| 32 | — | — | — | 17.2 | — | — |
| 48 | — | — | — | — | — | — |

—, the detected value is lower than the minimum quantification limit (1 μg/L).

TABLE 7

Main pharmacokinetic parameters of the compound of formula A after the SD rats in the reference preparation group are intragastrically administered with B capsule contents

| Parameter | $t_{1/2}$ (h) | $T_{max}$ (h) | Vd (L/kg) | CL (L/h/kg) | $C_{max}$ (μg/L) | MRT (h) | $AUC_{(0-\infty)}$ (μg/L*h) |
|---|---|---|---|---|---|---|---|
| No 1 | 2.15 | 6.00 | 40.88 | 13.16 | 295.00 | 8.05 | 3800.48 |
| No 2 | 2.11 | 6.00 | 27.54 | 9.06 | 491.00 | 7.57 | 5521.05 |
| No 3 | 2.27 | 6.00 | 63.79 | 19.51 | 284.00 | 7.82 | 2563.08 |
| No 4 | 2.07 | 8.00 | 27.04 | 9.06 | 459.00 | 8.85 | 5521.70 |
| No 5 | 1.95 | 8.00 | 11.15 | 3.95 | 1030.00 | 8.16 | 12649.33 |
| No 6 | 1.34 | 3.00 | 39.30 | 20.29 | 356.00 | 5.58 | 2464.65 |
| $\bar{x}$ | 1.98 | 6.17 | 34.95 | 12.50 | 485.83 | 7.67 | 5420.05 |
| SD | 0.33 | 1.84 | 17.72 | 6.43 | 279.60 | 1.11 | 3789.53 |

TABLE 8

Main pharmacokinetic parameters of the compound of formula A after the SD rats in the tested preparation group are intragastrically administered with C capsule contents

| Parameter | $t_{1/2}$ (h) | $T_{max}$ (h) | Vd (L/kg) | CL (L/h/kg) | $C_{max}$ (μg/L) | MRT (h) | $AUC_{(0-\infty)}$ (μg/L*h) |
|---|---|---|---|---|---|---|---|
| No 7 | 1.91 | 8.00 | 8.05 | 2.92 | 1370.00 | 7.95 | 17144.25 |
| No 8 | 1.93 | 6.00 | 8.64 | 3.11 | 1350.00 | 8.04 | 16086.30 |
| No 9 | 1.90 | 8.00 | 7.77 | 2.83 | 1370.00 | 8.63 | 17687.80 |
| No 10 | 1.33 | 8.00 | 4.85 | 2.53 | 1430.00 | 9.33 | 19795.40 |
| No 11 | 1.90 | 6.00 | 5.82 | 2.12 | 2350.00 | 7.18 | 23566.15 |
| No 12 | 2.08 | 6.00 | 22.19 | 7.41 | 633.00 | 7.63 | 6747.55 |
| $\bar{x}$ | 1.84 | 7.00 | 9.55 | 3.49 | 1417.17 | 8.13 | 16837.91 |
| SD | 0.26 | 1.10 | 6.36 | 1.95 | 546.67 | 0.76 | 5607.36 |

TABLE 9

Main pharmacokinetic parameter results

| Pharmacokinetic parameter | $t_{1/2}$ (h) | $T_{max}$ (h) | Vd (L/kg) | CL (L/h/kg) | $C_{max}$ mg/L | MRT (h) | $AUC_{(0-\infty)}$ (mg/L*h) |
|---|---|---|---|---|---|---|---|
| Reference preparation group | 1.98 ± 0.33 | 6.17 ± 1.84 | 34.9 ± 17.7 | 12.5 ± 6.43 | 485.83 ± 279.60 | 7.67 ± 1.11 | 5420.05 ± 3789.53 |
| Tested preparation group | 1.84 ± 0.26 | 7.00 ± 1.10 | 9.55 ± 6.36** | 3.48 ± 1.95** | 1417.17 ± 546.67** | 8.13 ± 0.76 | 16837.91 ± 5607.36** |

**P < 0.01 vs reference preparation group

From the above results, it can be seen that after the SD rats are intragastrically administered with B and C capsule contents, the exposure dose of the tested preparation group is higher than that of the reference preparation group, with its $AUC_{(0-\infty)}$ being 3.1 times that of the reference group, $C_{max}$ being 2.9 times that of the reference group, and F value being 310.66%.

Conclusion: after the SD rats are intragastrically administered with C capsules instead of B capsules, the compound of formula A is more distributed in body fluid, the clearance rate is lower, the exposure dose in rats is 3.1 times that of the B capsules, and the absorption is obviously higher than that of the B capsules.

The above embodiments are preferred embodiments of the present invention, but the embodiments of the present inventions are not limited by the foregoing embodiments. Any other changes, modifications, substitutions, combinations or simplifications made without departing from the spirit essence and principle of the present invention shall be equivalent replacements, and shall be included within the protection scope of the present invention.

What is claimed is:

1. A methanesulfonate polymorph of a 5-type phosphodiesterase inhibitor, the structure of the 5-type phosphodiesterase inhibitor being as shown in formula A:

Formula A wherein the methanesulfonate polymorph of the 5-type phosphodiesterase inhibitor includes the following diffraction peaks measured at 2θ reflection angles in an X-ray powder diffraction pattern: 7.1750°±0.2°, 7.6299°±0.2°, 8.8588°±0.2°, 13.2310°±0.2°, 14.3754°±0.2°, 14.8440±0.2°, 15.2941°±0.2°, 17.1838°±0.2°, 20.0314°±0.2°, 20.8507°±0.2°, 21.2839°±0.2°, 21.7890°±0.2°, 22.2594°±0.2°, 23.0373±0.2°, 25.1243°±0.2°, 25.4244°±0.2°, 26.1530°±0.2°, 28.1210°±0.2°, 30.0135°±0.2°, 31.4809°±0.2°, 32.3619°±0.2°, 37.2410°±0.2°, 37.6388°±0.2° and 40.8286°±0.2°.

2. The methanesulfonate polymorph of the 5-type phosphodiesterase inhibitor according to claim 1, wherein the X-ray powder diffraction pattern is shown in FIG. 1.

3. A preparation method of the methanesulfonate polymorph of the 5-type phosphodiesterase inhibitor according to claim 1, comprising the steps of: preparing a methanesulfonate of a 5-type phosphodiesterase inhibitor; and dissolving the methanesulfonate of the 5-type phosphodiesterase inhibitor into anhydrous ethanol, performing filter pressing after the solid is completely dissolved, cooling the filtrate to a temperature of 20° C. or lower and standing for crystallization.

4. The preparation method according to claim 3, wherein the step of preparing a methanesulfonate of a 5-type phosphodiesterase inhibitor is specifically: adding a compound of formula A to anhydrous ethanol, stirring uniformly, slowly adding 5% NaOH, stirring, performing suction filtration at a temperature of 10° C. or lower after the solid is completely dissolved, adding a mixed solution of methanesulfonic acid and anhydrous ethanol to the filtrate, adjusting the pH value to 7-8, stirring and crystallizing to precipitate a solid; performing suction filtration, adding the solid to anhydrous ethanol, heating to 30-35° C., adjusting the pH value to 3-4 with methanesulfonic acid, heating to 80° C., refluxing, then slightly cooling to 70° C., performing suction filtration while hot, naturally cooling the filtrate to room temperature, then cooling the filtrate to 15° C. or lower with ice water, standing for crystallization, performing suction filtration, and drying the solid at 80-90° C. to obtain a methanesulfonate of a phosphodiesterase 5-type inhibitor.

5. The preparation method according to claim 3, wherein the methanesulfonate of the 5-type phosphodiesterase inhibitor is dissolved in 3 times by weight of anhydrous ethanol and heated to 50-60° C., the pH value is adjusted to 3-4 with methanesulfonic acid, and then the mixed solution is heated to 70-75° C. so that the solid is completely dissolved.

6. An application of the methanesulfonate polymorph of the 5-type phosphodiesterase inhibitor according to claim 1 in preparation of a drug for treating male erectile dysfunction.

7. A pharmaceutical composition for treating diseases related to 5-type phosphodiesterase, comprising an effective amount of the methanesulfonate polymorph of the 5-type phosphodiesterase inhibitor according to claim 1.

8. A preparation method of the methanesulfonate polymorph of the 5-type phosphodiesterase inhibitor according to claim 2, comprising the steps of: preparing a methanesulfonate of a 5-type phosphodiesterase inhibitor; and dissolving the methanesulfonate of the 5-type phosphodiesterase inhibitor into anhydrous ethanol, performing filter pressing after the solid is completely dissolved, cooling the filtrate to a temperature of 20° C. or lower and standing for crystallization.

9. An application of the methanesulfonate polymorph of the 5-type phosphodiesterase inhibitor according to claim 2 in preparation of a drug for treating male erectile dysfunction.

10. The preparation method according to claim 8, wherein the step of preparing a methanesulfonate of a 5-type phosphodiesterase inhibitor is specifically: adding a compound of formula A to anhydrous ethanol, stirring uniformly, slowly adding 5% NaOH, stirring, performing suction filtration at a temperature of 10° C. or lower after the solid is completely dissolved, adding a mixed solution of methanesulfonic acid and anhydrous ethanol to the filtrate, adjusting the pH value to 7-8, stirring and crystallizing to precipitate a solid; performing suction filtration, adding the solid to anhydrous ethanol, heating to 30-35° C., adjusting the pH value to 3-4 with methanesulfonic acid, heating to 80° C., refluxing, then slightly cooling to 70° C., performing suction filtration while hot, naturally cooling the filtrate to room temperature, then cooling the filtrate to 15° C. or lower with ice water, standing for crystallization, performing suction filtration, and drying the solid at 80-90° C. to obtain a methanesulfonate of a phosphodiesterase 5-type inhibitor.

11. The preparation method according to claim 8, wherein the methanesulfonate of the 5-type phosphodiesterase inhibitor is dissolved in 3 times by weight of anhydrous ethanol and heated to 50-60° C., the pH value is adjusted to 3-4 with methanesulfonic acid, and then the mixed solution is heated to 70-75° C. so that the solid is completely dissolved.

* * * * *